United States Patent
Manzo et al.

[19]

[11] Patent Number: 6,083,529
[45] Date of Patent: *Jul. 4, 2000

[54] LIPOSOME ENCAPSULATED ACTIVE AGENT DRY POWDER COMPOSITION

[75] Inventors: Robert P. Manzo, Goshen, N.Y.; Jürgen Vollhardt, Holzminden, Germany; Nisha Malkan, Nanuet, N.Y.; Gary Friars, Midland Park, N.J.

[73] Assignee: Dragoco Gerberding & Co. AG, Germany

[ * ] Notice: This patent is subject to a terminal disclaimer.

[21] Appl. No.: 09/059,320

[22] Filed: Apr. 13, 1998

Related U.S. Application Data

[63] Continuation of application No. 08/962,906, Nov. 3, 1997, Pat. No. 5,783,211, which is a continuation of application No. 08/715,598, Sep. 18, 1996, abandoned.

[51] Int. Cl.$^7$ ............................ A61K 9/127; A61K 9/133
[52] U.S. Cl. ...................... 424/450; 424/484; 424/485; 424/488; 424/489; 424/490; 424/493; 424/496; 424/499; 424/500; 424/69

[58] Field of Search ....................... 424/450, 484, 424/485, 488, 489, 490, 493, 496, 499, 500, 69; 264/4.1, 4.3; 428/402.2

[56] References Cited

U.S. PATENT DOCUMENTS

| | | | |
|---|---|---|---|
| 4,708,861 | 11/1987 | Popescu | 424/1.1 |
| 4,766,046 | 8/1988 | Abra | 264/4.6 |
| 5,577,668 | 11/1996 | King | 239/559 |

*Primary Examiner*—Gollamudi S. Kishore
*Attorney, Agent, or Firm*—Pendorf & Cutliff

[57] ABSTRACT

A stable dry powder skin care powder having prolonged and controlled release properties, useful as baby powders, body talcs, deodorizing powders, OTC eczema preparations, foot powders, anti-fungal powders, etc. The dry powder is preferably prepared by a process comprising spray-drying a mixture of liposome encapsulated active agent, starch and maltodextrin. The particle is designed so that activity of, e.g., an anti-inflammatory agent such as Dragosantol® can be specifically triggered by skin conditions, such as moisture, for optimal timing of delivery.

12 Claims, 1 Drawing Sheet

6,083,529

LIPOSOME ENCAPSULATED ACTIVE AGENT DRY POWDER COMPOSITION

REFERENCE TO RELATED APPLICATIONS

This application is a continuation of application Ser. No. 08/962,906 filed Nov. 3, 1997, now U.S. Pat. No. 5,783,211, which is a continuation of application Ser. No. 08/715,598 filed Sep. 18, 1996, abandoned.

BACKGROUND OF THE INVENTION

1. Field of the Invention

The invention relates to dry powder skin care compositions useful as baby powders, body talcs, deodorizing powders, OTC eczema preparations, foot powders, antifungal powders, etc. More particularly, the invention relates to stable dry powders having prolonged and controlled release properties. The dry powder is preferably prepared by a process comprising spray-drying a mixture of liposome encapsulated active agent, modified starch and maltodextrin. The particle is designed so that activity of, e.g., an antiinflammatory agent such as Dragosantol® can be specifically triggered by skin conditions, such as moisture, for optimal effect.

2. Description of the Related Art

Prevention of diaper dermatitis, i.e., diaper rash, involves keeping a baby's delicate skin dry and free of irritants. Topical powders having drying properties, referred to herein as dry powders, are commonly applied to assist in physically absorbing moisture and preserving skin dryness. Drying powders are typically either corn starch based or talcum based. However, corn starch may be irritating to sore skin, and baby talcum powder can be harmful to an infant's lungs if inhaled during diaper changing.

In comparison to the above-described physically acting topical composition, another type of skin care product is based upon a pharmaceutical agent which must usually be delivered via a specially formulated topical composition. For example, bisabolol is a biologically active agent known to have antiphlogistics and antibacterial properties. When used in a product in a standard formulation, the whole amount of bisabolol is released at the time of application; so there is an initial burst of activity which phases out quickly. In order to delay and prolong the release of such fast acting pharmaceutical agents, it is known to incorporate these active substances in microcapsules or matrices.

However, neither of these approaches alone is satisfactory in conditioning the skin. Even when both approaches are used in combination they may not provide the greatest amount of active agent at the precise time of greatest need. Consumers are becoming increasingly educated and expect a high level of sophistication in their products. There is thus a need for an intelligent skin care product which can provide not only physical absorbency of moisture and prolonged release of active agent, but which also coordinates peak delivery of active agent to a particular biological demand, such as skin wetness. This responsive delivery is referred to herein as controlled delivery. A baby powder product recently marketed by CreativeCare BabY Line [sic] uses ultra refined oat particles medicated with zinc oxide, a mild neutralizer and astringent, as "micro-sponges" with natural anti-itch and anti-irritant properties. However, there is room for improvement in the feel and controlled efficacy of the product.

In recent years increasing attention has been paid to the development of liposomes for use as "containers" for substances which are intended to be liberated upon reaching a target site. Liposomes are small, closed vesicles formed from lipids, usually phospholipids. Lipids generally have a hydrophobic "tail" and a hydrophilic "end". When mixed with water, hydrophobic ends tend to join toward a common center while the hydrophobic tails become oriented outwardly to interface with the water. The lipids may form a monomolecular layer or may arrange themselves in more than one layer of lipids, to form a "liposome" having an inner space and an outer surface. Liposomes may also have more than one layer.

Liposomes have been used to deliver active agent to the skin. For example, U.S. Pat. No. 5,128,139 (Brown et al.) teaches a deodorant comprising liposomes containing grapefruit seed extract. The bioactive agents are entrapped within multilamellar liposomes complexes to provide release over time. Brown et al. acknowledge that liposomes are inherently unstable and tend to break apart, releasing the contents within. Brown et al. thus layers the liposomes or forms them into clusters such that the liposomes which are confined within or are sandwiched between outer layers of liposomes are protected and are more likely to remain stable. The outer liposomes tend to break apart releasing their contents while protecting the inner liposomes for later degradation and release. While the product provides for prolonged release of active agent, there is no discussion of controlled release, i.e., timing release so as to peak when needed.

U.S. Pat. No. 4,937,078 to Mezie et. al. discloses the incorporation of topical anesthetic actives into liposomes which essentially encapsulate the active ingredient within layers of lipid material. It is reported that the lipid vesicles provide a more pronounced cutaneous anesthetic or analgesic effect while employing less of the topical anesthetic agent. The lipid vesicles allegedly provide a means of prolonging the permeation rate without the risk for discomfort due to numbness or systemic reactions. However, prolonging release simply refers to constant rate of release over an extended period of time. There is no mention of masking active agent until need, then releasing an amount of active agent commensurate with the need.

U.S. Pat. No. 5,510,120 (Jones, et al.) teaches a cosmetic composition for topical application to the skin and/or hair. The composition comprises particles (microcapsules or liposomes) which enclose a cosmetically-effective benefit agent (e.g., an agent intended to modify or enhance body odor) active at a target location accessible by application to the skin and/or hair. The particles have means, namely lectin, for binding to targeted microorganisms present on the skin and/or hair, for example those bacteria responsible for skin disorders, scalp irritation, and underarm and foot odor. The encapsulated active agent may be "combined" with a vehicle or carrier such as water, various liquid substances, and various powders such as chalk, talc, fullers earth, kaolin, starch, gums, colloidal silica, sodium polyacrylate, tetra alkyl and/or trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, ethylene glycol monostearate.

While Jones et al. teach targeting delivery of active agent in terms of location, they do little to target delivery in terms of time, i.e., controlling release to peak at the time of greatest need.

U.S. Pat. No. 4,508,703 (Redziniak et al.) teaches a method of preparing a pulverulent mixture of amphiphilic lipidic constituents (e.g., phospholipids) by adding fine solid microalveolate particles (such as kieselguhr) and atomization (col. 6, lines 40–45). The particles are then rehydrated to produce hydrated lipidic lamellar phases. There is, however, no mention of applying a powder to skin.

Accordingly, there remains a need for a new type of delivery system which satisfies a number of requirements, namely, it must be capable of formulating even labile compounds, it must provide enhanced stability, it must be aesthetically pleasing, it must increase efficacy, and it must have reduced irritancy, it must remain in place, and most importantly, it must remain capable of releasing active ingredient in response to biological demand.

SUMMARY OF THE INVENTION

It is an object of the present invention to provide a pharmaceutical or cosmetic delivery system which provides moisture absorbency as well as controlled release of active agent, such as an anti-inflammatory agent.

Another object of this invention is to provide combined moisture absorbency via starch and improved controlled treatment benefits of incorporated ingredients like Dragosantol® and Farnesol or any other active agent.

Another objective of this invention is to deliver ingredients to the skin, which help to maintain an intact skin function in relation to a proper skin barrier and skin-pH-Value.

Another objective of this invention is to protect the active ingredients from degradive processes like oxidation in comparison to common dry application forms where the active is distributed on a large surface area on the particles of a carrier system, e.g. native starch or silica gel.

Another objective of this invention is to provide baby powders, body talcs, eczema products, antiperspirant powders, dry deodorizing powders, etc. with dual benefits of moisture absorbency and skin care.

These objectives are achieved by encapsulating active agents in liposomes, preferably nanosomes having an average diameter of approximately 200 nm, which are then mixed and spray dried with a carrier or matrix forming composition, preferably a water absorptive composition such as modified starch and preferably also maltodextrin. Liposomes act as the delivery agents for active agents like Dragosantol®, Farnesol, etc. Dry powders like talc, starch, starch esters, zinc oxide, lithium carbonate, lithium stearate, aluminum stearate, magnesium stearate, magnesium carbonate, etc. are used not only for their traditional functions as absorbents but also as sensitizers for triggering the release of active agent. That is, as the water absorbent component of the particles according to the present invention absorbs water, it acts as a catalyst on the liposome component, which is physically adsorbed into or otherwise intimately associated with the absorbent as a result of the mixing and spray drying process, triggering a loss of structural integrity in the liposome carrier followed by the release of liposomes and of the active agent. Thus, in response to a condition such as perspiration or diaper wetting, the particles according to the present invention release one or more of, e.g., an anti-perspirant, anti-microbial or anti-inflammatory agent.

In a preferred embodiment the particles are formed by a process wherein active substance is mixed with lecithin to form liposomes (actually nanosomes, 200 nm in size) under action of a high pressure high shear force homogenizer. At this stage the product looks like milk, and a carrier substance, namely, a blend of maltodextrin (a polysaccharide between detrin and maltose) and modified starch, is mixed in under low shear force mixing. Before spray drying the pH-value could be adjusted to about. 5.0, if neccessary. The mixture is spray dried to form unregular, off white particles.

The bioactive agent-bound liposome composition disclosed herein may be used in many topical applications including baby powders, body talcs, deodorizing powders, OTC eczema preparations, foot powders, anti-fungal powders, deodorant soaps, cosmetic preparations, etc.

The foregoing has outlined rather broadly the more pertinent and important features of the present invention in order that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other biologically active agent delivery systems for carrying out the same purposes of the present invention. It should also be realized by those skilled in the art that such equivalent structures and the processes for forming them do not depart from the spirit and scope of the invention as set forth in the appended claims.

BRIEF DESCRIPTION OF THE DRAWINGS

For a fuller understanding of the nature and objects of the present invention reference should be made by the following detailed description taken in with the accompanying drawings in which.

DETAILED DESCRIPTION OF THE INVENTION

Figure 1:
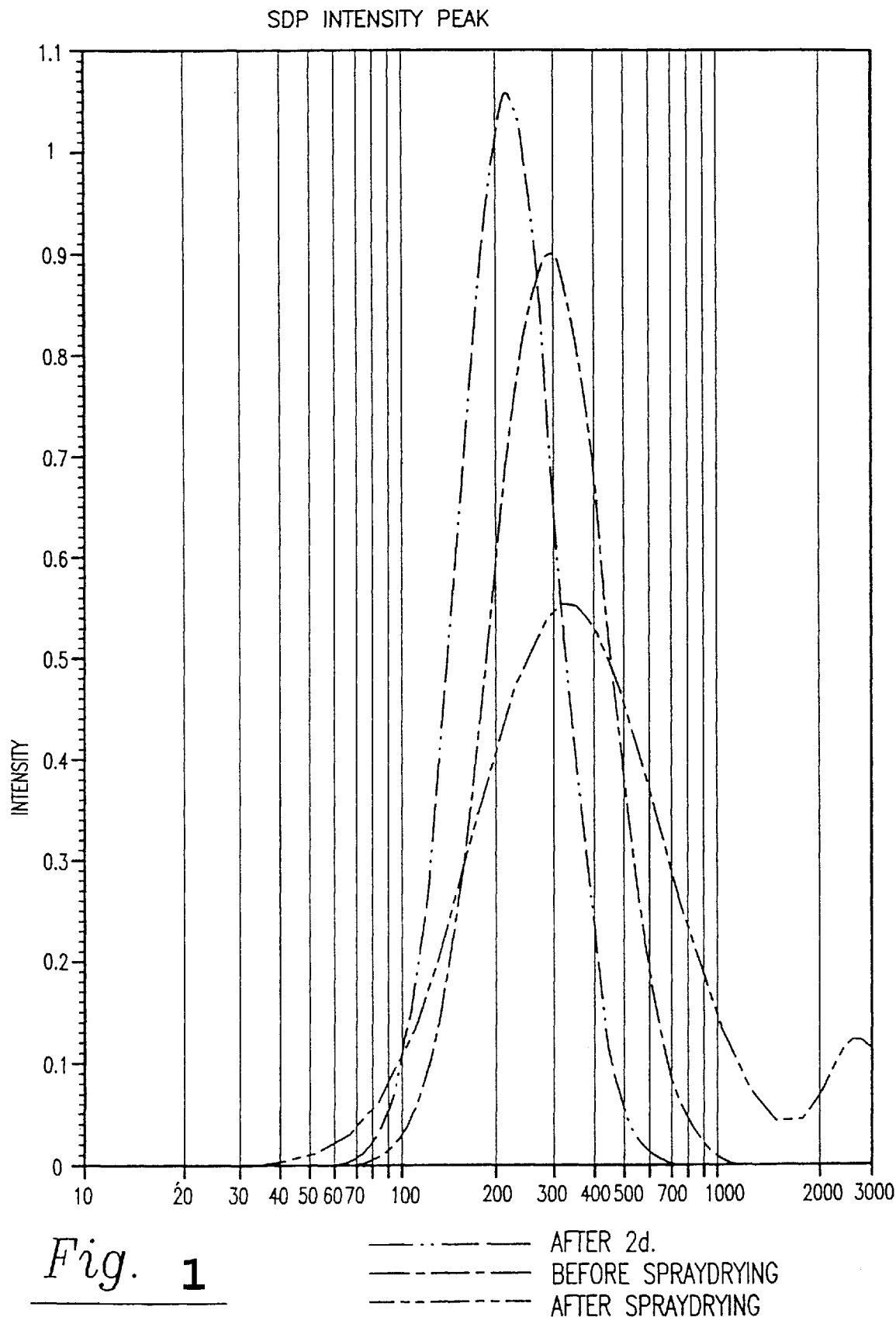
FIG. 1 shows particle size measured by laser scattering after each of nanoparticle dispersion, nanoparticle encoating, and spray drying steps followed by rehydration of the product powder in Example 3.

The delivery system of the present invention can be variously formulated so long as the product comprises active agent at least partially encapsulated in liposomes, which liposomes are in turn physically or chemically adsorbed onto or dispersed within a conventional dry powder carrier or matrix in such a way that the dry powder carrier or matrix protects and stabilized the liposomes while dry, and that absorption of water by the dry powder triggers release of active agent from the liposome.

One specific example of a dry powder composition according to the present invention is a powder which contains α-bisabolol (the main ingredient in a composition available under the tradename DRAGOSANTOL® from Dragoco Corporation, Totowa, N.J.) as the active ingredient. Bisabolol is known to have antiphlogistic and antibacterial properties, and is generally applied to the skin in the form of a solution or in form of emulsion systems. In accordance with the present invention bisabolol is incorporated in liposomes, and the liposomes are mixed with a starch-based carrier system and spray dried to form Starchosomes™ wherein the conventional aqueous phase of liposome is up to more than 95% removed and replaced with a starch-based carrier system. The carrier (i.e., modified starch and maltodextrin) is a moisture absorbent which, upon absorbing moisture, triggers the mechanism for the elution of the bisabolol onto the skin. So long as the powder remains dry, the liposomes remain stable and active ingredient is preserved. As the powder absorbs increasing amounts of moisture, increasing amounts of active agent are released. This relationship provides a stable, long lasting, controlled anti-inflammatory property to the powder which is very useful in baby powders, eczema preparations, foot powders, etc. where cornstarch can absorb moisture and release bisabolol to fight irritation.

While liposomes, especially those prepared from lecithin extracts, are preferable for the purposes of carrying out the present invention, micelles encapsulating active agents may be prepared from various non-polar materials in accordance with standard practices known to those skilled in the art of emulsion chemistry. Such micelles may be formed from naturally occurring oils, fats, or the like.

Biologically Active Ingredient

The dry powder formulation according to the present invention is in no way limited to bisabolol, and can be used to provide controlled delivery of an extensive array of pharmaceutically or biologically active agents.

A second specific example of a desirable controlled release substance is farnesol (3,7,11-trimethyl-dodeca-2,6,10-triene-1-ol). As taught in U.S. Pat. No. 4,220,665 (Klein), farnesol is highly effective in inhibiting growth of odor forming bacterial flora of the skin at relatively low concentrations.

Other suitable active agents include anti-perspirant, astringents, anti-inflammatory, anti-microbial, anti-fungal, etc. as well known in the art. The active agent, after incorporation and spray drying, should preferably but not necessarily be in a dry powder form.

It is not necessary that all active ingredient present in the dry powder product be encapsulated in the liposomes. Some free active agent may be added to give some immediate action effect.

The various active agents which can be incorporated in the dry powder according to the present invention are too numerous to list. See, for example, U.S. Pat. No. 5,446,070 (Mantelle) which teaches topical administration of pharmaceutically active agents, which agents may be microencapsulated. Mantelle provides at columns 23–41 a very extensive list of anesthetic type drugs which may be microencapsulated with liposomes. These anesthetic type drugs are only one class of active agent which can be formulated into the dry powder of the present invention.

Liposome Formation

Liposome encapsulation of biologically active agents is a well known technique and reference may be made to a wealth of patents and scientific and trade texts teaching liposome formation and active agent encapsulation. The present invention is not limited to any particular liposome size or construction, but unilamellar liposomes with a particle size of less than 400 nm are preferred. The liposomes most preferably have a particle size range of 100 to 300 nm, with an average particle size of about 200 nm (i.e., at least 50% by volume of encapsulated active agent is preferably encapsulated in liposomes having a diameter of from 100 to 300 nm, more preferably 150 nm to 250 nm).

Liposomes are formed when suitable amphophilic molecules are allowed to swell in water or aqueous solutions to form liquid crystals usually of multi-layer structure comprised of many bilayers separated from each other by aqueous material (also referred to as coarse liposomes). A type of liposome consisting of a single bilayer encapsulating aqueous material is referred to as a unilamellar vesicle. If water-soluble materials are included in the aqueous phase during the swelling of the lipids they become entrapped in the aqueous layer between the lipid bilayers. Water-soluble active ingredients such as bisabolol can thus be encapsulated in the aqueous spaces between the molecular layers. The pre-liposomal phospholipid mixture may also contain a number of other natural substances such as carotinoids and vitamins.

Although the lipids used in the present invention for producing the liposome component may be derived from any number of sources, a particularly suitable source is lecithin, such as purified soya lecithin. A phosholipid fraction derived from lecithin, e.g. soya lecithin, which is high in phosphatidylcholin and therefore particularly suitable for use in the invention is preferred. Phosphatidylcholin (PC) improves the stability of the liposome vesicles and is especially advantageous in promoting healthy cell maintenance and growth. The Phosphatidylcholin content of the lecithine mixture may vary, but should be about 60–85%, preferably 70–80%, most preferably about 75%. The phosphatidylethanolamine (PE) content of the mixture may also vary, but a preferred percentage is from about five percent to about twenty-five percent of the mixture by weight. The content in Lysophosphatidylcholin should be as low as possible in order to increase stability of liposomes. A content of less than 6% within the total Lecithin fraction is preferred. Phosphatidylcholin and PE enhance the hydrophobic nature of the formed liposomes and enhance the stability of the liposomes. Liposomes which contain PC and PE in the surface structure resemble lipid membranes found in nature. PC and PE delivered to the skin helps the skin to maintain their barrier function.

The encapsulation of active compounds can be achieved by a number of methods. The method most commonly used involves casting a thin film of phospholipid onto the walls of a flask by evaporation from an organic solvent. When this film is dispersed in a suitable aqueous medium, multilamellar liposomes are formed. Upon suitable sonication, the coarse liposomes from smaller similarly closed vesicles.

As indicated above, the incorporation of active agent in liposomes is well known and reference may be made to a variety of patents and treatises. For example, liposomes or lipidic particles can be prepared in accordance with U.S. Pat. No. 5,077,057 (Szoka , Jr.). Liposomes formed from nonphosphal lipid components which have the potential to form lipid bilayers is disclosed in Biochim. Biophys. Acta., 19:227–232 [1982]. A general discussion of techniques for preparation of liposomes and of medication encapsulating liposomes can be found in U.S. Pat. No. 4,224,179 (Schneider).

A great number of patents teach encapsulation of active agent into liposomes for topical application, but no patent teaches a dry powder formulation. For example, U.S. Pat. No. 5,356,633 (Woodle, et al.) teaches the preparation and injection of a liposome-entrapped anti-inflammatory agent. Great detail is given on the method for compound loading, i.e., the method for incorporation of compound into liposomes. U.S. Pat. No. 5,376,380 (Kikuchi, et al.) teaches a process for forming drug containing liposomal products, the process comprising freeze drying or spray drying empty liposomes, then adding an aqueous solution of a drug to the freeze dried or sprayed dried liposomal preparation for reconstitution.

U.S. Pat. Nos. 5,446,070; 5,332,576 and 5,234,957 (Mantelle) teach topical administration of pharmaceutically active agents, which agents may be micro-encapsulated. U.S. Pat. No. 5,447,930 (Nayak) discloses the use of liposomal encapsulation to provide a means for controlling the permeation rate of topical anesthetic actives. U.S. Pat. No. 5,470,579 (Bonte, et al.) incorporates xanthine into liposomes for promoting pigmentation. U.S. Pat. No. 5,476,852

(Cauwenbergh) teaches the topical administration to subjects suffering from acne. Cyclodextrin may be encapsulated in liposome. There is no mention of dry powder. U.S. Pat. No. 5,514,374 (Bonte, et al.) teaches a dermatological composition for promoting skin pigmentation or preventing build-up of body fat. The active ingredient is black horehound which can be incorporated into liposomes (column 6, line 18). There is no mention of dry powder.

U.S. Pat. No. 5,514,712 (LeClere) encapsulates oils of chaulmoogra in mono- or plurilamellar liposomes. U.S. Pat. No. 5,519,020 (Smith, et al.) teaches topical application of liposome encapsulated nitrate oxide for promotion of wound healing. There is teaching only of adhesives and bandaging pads. There is no mention of dry powders. U.S. Pat. No. 5,476,651 (Meybeck, et al.) encapsulates extract of Cyperus in liposomes for a dermatological composition. U.S. Pat. No. 5,034,228 (Meybeck, et al.) relates to a composition comprising hydrous lipidic lamellar phases or liposomes containing, as an active agent a retinoid or a structural analogue of retinoid, such as a carotenoid or retinoin. There is a discussion of preparation of liposomes, including lyophilization techniques. U.S. Pat. No. 4,942,038 (Wallach) teaches a new humectant for animal care product use having a moisturizer encapsulated in a lipid vesicle. The humectant is particularly useful as an additive to shampoos or cream rinses.

U.S. Pat. No. 5,188,837 (Domb) teaches a microsuspension system and method for its preparation. The microsuspension contain liposheres, which are solid, water-insoluble microparticles that have a layer of a phospholipid embedded on their surface. The core of the liposphere is a solid substance to be delivered, or a substance to be delivered that is dispersed in an inert solid vehicle, such as a wax. The final preparation may be lotion or spray for topical use (column 3, line 33). U.S. Pat. No. 4,946,683 (Forssen) provides an extensive discussion of liposome-entrapped drug compositions, but does not discuss topical administration of the end product or a dry powder formation.

U.S. Pat. No. 5,169,631 (Rase et al.) teaches a topical deodorant antiseptic composition comprising microcapsules containing an antimicrobial agent. The deodorant compositions may be applied to the armpits or feet in the form of sticks, gels or powders (col. 2, line 54). Example 2 is a foot powder composition comprising mainly microcapsules, zinc stearate, polyamine-12, and talc. The microcapsules are formed of cross-linked collagent and glycosaminoglycan. There is no mention of liposomes, and no teaching of mixing and spray drying to form a powder with liposomes chemically or physically adsorbed onto or contained in a dry powder carrier or matrix.

U.S. Pat. No. 5,137,725 (Handjani et al.) teaches a cosmetic or pharmaceutical composition comprising lipidic spherules which may contain antiperspirants, deodorants, or astringents (col. 5, line 60) or anti-inflammatories, antibiotics or bactericides (col. 6, lines 4–5). There is no mention of a dry powder formulation.

A liposome suspension for forming large liposomes (0.1 to 10 um) can be prepared by any of the standard methods for preparing and sizing liposomes. These include hydration of lipid films, solvent injection, reverse-phase evaporation and other methods, such as those detailed in Ann. Rev. Biophys. Bioeng. 9:467 (1980). Reverse-phase evaporation vesicles (REVs) prepared by the reverse-evaporation phase method is described in U.S. Pat. No. 4,235,871, incorporated herein by reference. The preparation of multilamellar vesicles (MLVs) by thin-film processing U.S. Pat. No. 4,737,923, incorporated by reference. Basically, a mixture of liposome-forming lipids is dissolved in a suitable solvent is evaporated in a vessel to form a thin film, which is covered by an aqueous buffer solution. The lipid film hydrates to form MLVs, typically with sizes between about 0.1 to 10 ums.

The REVs or MLVs may be further treated to produce a suspension of smaller, substantially homogenous liposomes, in the 0.02–2.0 um size range. One effective sizing method involves extruding an aqueous suspension of the liposomes through a polycarbonate membrane having a selected uniform pore size, typically 0.2 um Ann. Rev. Biophys. Bioeng., 9:467 (1980). The pore size of the membrane corresponds roughly to the largest sizes of liposomes produced by extrusion through that membrane, particularly in which the preparation is extruded two or more times through the same membrane. Thus, this technique may yield liposomes for which a better term may be nanosomes because they have a size as small as 200 nm.

Non-biologically Active Ingredients

A fragrance may be added to the liposome composition. When fragrance is added during the formation of liposomes, the liposomes entrap the fragrance, and the fragrance is subject to periodic or controlled release. As a result, the fragrance will last longer than unencapsulated fragrance. A highly volatile fragrance is not preferred. Rather, in the case that fragrance is encapsulated in liposome, it is preferred that the fragrance remain encapsulated and inert so long as the liposome and dry powder remain dry, and is released as the liposome is exposed to moisture.

The amount of fragrance included in the composition may vary, but a preferred amount of fragrance is about 0.5% to about 3% of the total weight of the material encapsulated in the composition. Quantities of fragrance outside of this preferred range may also be used, as well as significantly larger amounts.

Powder Matrix and Spray Dry Carrier

The powders which may be used in the present invention as carrier or matrix may be any powders conventionally used as dry powders (i.e., skin compatible powders having an ability to absorb moisture and impart a dry feeling to skin). The powders may be selected from chalk, talc, fullers earth, kaolin, starch, gums, colloidal silicon dioxide, sodium polyacrylate, tetra alkyl and/or trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, ethylene glycol monostearate.

The dry powder composition according to the invention can also optionally comprise a perfume or fragrance additive external to the liposomes in an amount sufficient to make the composition acceptable to the consumer and pleasant to use. Usually, the perfume will form from 0.01 to 10% by weight of the composition.

Powders which absorb water but can not be solubilized are used as carriers. Powders which can be solubilized in water may be used as carriers but are preferably solubilized in water and mixed with liposome to form a protective matrix around the liposomes prior to spray drying. Such soluble powder materials include gums, proteins protein hydrolysates, (preferably gelatin which has been hydrated and rigidified with maltodextrin), and starches.

A hydrocolloid such as xanthan, maltodextrin, galactomanan or tragacanth, preferably maltodextrin, is preferably also included in the powder forming composition. Starch, or a starch/maltodextrin mixture, is the preferred matrix or carrier for use in the present invention.

For starch preparation and encapsulation techniques, reference may be made to, e.g., U.S. Pat. No. 4,911,952 (Doane et al.) and U.S. Pat. No. 4,859,377 (Shasha et al.).

Starch is a low-cost and abundant natural polymer composed amylose and amylopectin. Amylose is essentially a linear polymer having a molecular weight in the range of 100,000–500,000, whereas amylopectin is a highly branched polymer having a molecular weight of up to several million. When starch is gelatinized in water and cooled, the amylose retrogrades to a much greater extent than the amylopectin fraction. Retrogradation is a term applied to the phenomenon whereby starch chains in dispersion associate, become insoluble, and precipitate. The rate and extent of retrogradation depend on properties of dispersion (pH, temperature, concentration) and on the amount of amylose present in the dispersion.

Common cornstarch (pearl) contains about 25% amylose and 75% amylopectin; whereas the waxy corn starches contain only amylopectin, and those referred to as a high-amylose starch contain up to 75% amylose. Common corn starch, acid modified, is preferred in the present invention. The starch may also be a high protein flour comprising 40% starch and 60% protein as disclosed in U.S. Pat. No. 3,786,123.

The starting encapsulating material for use in the invention includes any pregelatinized starch which will retrograde to form a gel upon rehydration in an aqueous medium. Encapsulation of the liposome encapsulated biologically active agent into the starch matrix is initiated by uniformly dispersing the liposomes throughout an aqueous dispersion of the geletanized starch. The order of combining the formulation is not critical and may be conducted in what manner best facilitates the process. Under suitable gelation conditions the starch which has been dispersed in an aqueous medium begins to retrograde, thereby forming a gelatinous mass. By proper formulation as discussed below the dispersion will gel and can thereafter be taken to dryness. The reassociation of the amylose components of the starch results in a substantially homogeneous starch matrix in which, now, liposome encapsulated active agent is uniformly dispersed throughout.

Pregelatanized starches are commercially available and are prepared for example by cooking the starch at elevated temperatures and pressures in the presence of a lower alcohol. It is preferred that the pregelatinized starch be cold-water-swelling, and especially preferred that it be a chemically modified starch, such as a starch modified with a mild acid selected from the group consisting of malic acid, tartaric acid, citric acid, maleic acid and succinic acid, of which succinic acid modified starch is most preferred. The level of amylose in the starch is preferably above about 5%, below which the starch will not form a cohesive mass in the presence of water.

The starch is prepared for encapsulation by thorough dispersion in water under conditions that completely disrupt the starch granules and completely disassociate essentially all the amylose molecules without significant depolymerization. Such dispersion is accomplished with starches having amylose contents of up to about 25% when an aqueous slurry of the starch is passed through a steam-injection cooker at a temperature of about 120°–135° C. Starches having greater than about 25% amylose require temperatures of about 155°–160° C. Gelatination at lower temperatures does not allow complete granule rupture, while gelatinization at higher temperatures causes some starch depolymerization. Steam-injection cooking is a preferred method of gelatinization because it affords the advantage of providing a continuous process and because disruption of starch granules is accomplished rapidly and completely in one step. However, in order not to unduly disrupt liposomes, gelatinized starch should be cooled somewhat prior to combining starch and liposome.

Alternatively, extrusion cooking will effectively achieve the gelatinization. For purposes of this invention, the starch dispersion is considered to be in the aqueous phase, which constitute the continuous phase of the system for encapsulation of liposome. The specified starches prepared in this manner are effective to achieve encapsulation without the presence of any additional encapsulating agent.

Though the above discussion refers to pearl cornstrach, it is understood that other natural granular starches could be pregelatinized for purposes of the invention. These would include the other cereal starches, potato starch, tapioca starch, flours containing these starches, as well as mixtures of these with waxy cornstarch and high amylose cornstarch.

Maltodextrin is preferably added to starch and forms a hydrocolloid surface upon the spray dried particles produced in accordance with the present invention. Maltodextrin is well known in the food industry, and reference may be made to U.S. Pat. Nos. 5,039,540; 5,260,304; 5,428,150; and 5,431,951 for maltodextrin processing.

Encapsulation is accomplished without the use of any chemical additives or modifiers by the simple and convenient process of dehydrating or drying the starch-agent mixture under conditions that allow the amylose components of the starch to reassociate. The result is a substantially homogenous mass analagous to the precursive mixture in which, now, discontinuous domains of active ingredients are uniformly dispersed throughout a continous matrix. This process distinguishes from microencapsulation which yields discrete particles, each comprising a domain of agent enveloped by a film or coating of encapsulating agent.

The recovery procedure is aimed at converting the homogenous mass to discrete, free-flowing, nonagglomerating particles. In accordance with one method of recovery contemplated herein, the starch-liposome encapsulated agent mixture is placed on trays and dried at 30° C. for 90 min. The resulting film is readily ground into small, nonagglomerating particles.

In an more preferred embodiment, the starch-liposome encapsulated agent mixture is worked in a sigma-blade mixer under a stream of air until sufficient moisture is lost that crumbling occurs. The resulting particles may be easily washed, filtered, dried, and further ground if necessary by any conventional methods. In some cases further grinding is not necessary. Dewatering can also be conducted in an extruder.

Most preferred, however, is spray drying in a manner well known in the art. The precise manner in which the starch, liposomes and maltodextrin associate during spray drying is not yet precisely understood and varies depending upon processing parameters. Although some effort is made herein to explaining what is presently known or suspected about these unique particles in order to advance the state of the art, the present inventors do not wish to be bound by any of these explanations and the explanations may be considered as hypothesis. The delivery system according to the present invention is made by following the process described herein, and an understanding of the precise structure produced thereby is not essential to working the invention.

The following examples are illustrative of the present invention and are not intended to be limiting.

EXAMPLE 1

A liposome composition was prepared by adding one (1) milliliter (ml) of ethanol to 0.25 grams of preliposome phospholipid mixture. The addition of ethanol to the preliposome phospholipid mixture is a solvating step which helps to loosen the phospholipid in the mixture.

The mixture as then co-solubilized with 0.8 grams of α-bisabolol. The mixture was stirred. Finally, four milliliters of distilled water was added to the mixture and mixed rapidly. The addition of distilled water caused the lipid fraction of the mixture to form liposome vesicles.

The liposomes were mixed with a water solution of succinic acid modified starch and spray dried to form spray dried liposome coated starch particles where the α-bisabolol (Dragosantol®) is encapsulated at 20% in the liposome. This product is referred to as starchosome.

EXAMPLE 2

The starchosome of Example 1 was mixed with conventional baby powder ingredients as follows:

|  | Ingredient | % |
| --- | --- | --- |
| 1) | Aluminum Starch Octenyl Succinate | 68.00 |
| *2) | Starchosomes ™ | 2.00 |
| 3) | Zinc Oxide | 10.00 |
| 4) | Lithium Stearate | 10.00 |
| 5) | Magnesium Stearate | 10.00 |

Starchsomes are the spray dried liposome coated starch particles where the α-bisabolol (Dragosantol®) is encapsulated at 20% in a liposome and coated on to starch particles.

EXAMPLE 3

This Example further illustrates the principle of the manufacturing process by demonstrating production of a spray dried nanoparticle with α-bisabolol as the dry powder delivery system according to the present invention. The product is produced by a three step process:

1. Nanoparticle Dispersion, 1st Formulation 625 g Dragosantol® (containing >85% α-Bisabolol), 1.7 g Tocopherol and 105 g purified Soya Lecithine (Nat 8539, Rhone-Poulenc Rorer) are used to form a preemulsion with 1768 g water through mechanical stirring. This preemulsion is homogenized with a high pressure homogenizer (Rannie, Model Mini Lab, Typ 8.30H, at 20–60° C. and 500–800 bar pressure to form a nanoparticle dispersion with an average droplet size of between 100 and 1000 nm, preferably about 200 nm.

1. 2. Nanoparticle Dispersion, 2nd Formulation 80 g Dragosantol® (containing >85% α-Bisabolol), 0.2 g Tocopherol, 14 g purified Soya Lecithine (Nat 8539, Rhone-Poulenc Rorer) and 0.7 g Potassium Cetyl Phosphate (Amphisol K, Givaudan) are used to form a preemulsion with 175 g water through mechanical stirring. This preemulsion is homogenized with a high pressure homogenizer (Rannie, Model Mini Lab, Type 8.30H, at 20°–60° C. and 500–800 bar pressure to form a nanoparticle dispersion with an average droplet size of between 100 and 1000 nm, preferably about 200 nm.

1. 3. Nanoparticle Dispersion, 3rd Formulation 840 g Dragosantol® (containing >85% α-Bisabolol), 2.8 g Tocopherol and 140 g purified Soya Lecithine (Nat 8539, Rhone-Poulenc Rorer) are used to form a preemulsion with 1800 g water through mechanical stirring. This preemulsion is homogenized with a high pressure homogenizer (Rannie, Model Mini Lab, Typ 8.30H, at 20°–60° C. and 500–800 bar pressure to form a nanoparticle dispersion with an average droplet size of between 100 and 1000 nm, preferably about 200 nm.

2. Nanoparticle Encoating and Spray Drying Carrier Addition

The nanoparticle dispersion produced in the first step is mixed with a water solution of modified starch (Capsul E, National Starch). Then, maltodextrin 18–20 (Roquette, Frankfurt) is added to the solution. The pH-value was adjusted to between 3 and 6, preferably 4.5 to 5.5, by adding sodium hydroxide solution.

3. Spray Drying

By spray drying in a conventional manner, the water content of the above mixtures is reduced through evaporation of water to form a white powder. By adding various amounts of maltodextrin or starch to the Nanoparticle disspersion the α-Bisabolol content could be varied between 1–50%, preferable 25–40%.

The particle size was measured by laser scattering after step 1, step 2 and step 3 followed by rehydration of the product powder, and the results are shown in FIG. 1. It could be seen that the particle size slightly increases in step 2 and that comparable particles could be found after spray drying and rehydration.

As a result of experimentation and skin testing it was determined that the particle size of the spray dried powder should preferentially be between 20–80 um, and particle size could be adjusted by the way of spray drying. The particles were also found to have an irregular shape. The product appears to be an off white powder, with a characteristic low odor, and with an α-Bisabolol content of 20–25% by weight and a water content of <5%. The particles should have a maximum peroxide value of up to 4. The preferred value is 0.

Although the dry particle composition was first designed as an improved delivery vehicle for controlled delivery of a pharmaceutical agent to the epidermis, it will be readily apparent that the device is capable of use in a number of other applications, such as for preserving clothes where it may be necessary to release mold preventative, or as an ingredient incorporated directly in a diaper, etc.

Although this invention has been described in its preferred form with a certain degree of particularity with respect to starch encapsulated bisabolol, it is understood that the present disclosure of the preferred form has been made only by way of example and that numerous changes in the details of structures and the composition of the combination may be resorted to without departing from the spirit and scope of the invention.

What is claimed is:

1. A spray dried body powder comprising starch, a hydrocolloid gum, and liposomes containing biologically active agent in their aqueous interior.

2. A spray dried body powder composition as in claim 1, wherein said hydrocolloid gum is selected from the group consisting of xanthan, maltodextrin, galactomanan and tragacanth.

3. A spray dried body powder as in claim 2, wherein said liposomes have a droplet size of from 100 to 1000 nm.

4. A spray dried body powder as in claim 2, wherein said liposomes have a droplet size of from 200 to 300 nm.

5. A spray dried body powder composition as in claim 1, wherein said starch is an acid modified starch.

6. A spray dried body powder composition as in claim 5, wherein said acid modified starch is partially neutralized.

7. A spray dried body powder composition as in claim 1, wherein said hydrocolloid gum is maltodextrin.

8. A spray dried body powder composition as in claim 1, wherein said dry powder has a particle size in the range of 20–80 μm.

9. A spray dried body powder composition as in claim 1, wherein said dry powder has a particle size in the range of 30–50 μm.

10. A spray dried body powder composition as in claim 1, wherein said biologically active agent is selected from the group consisting of anti-inflammatory, antiphlogistic, antibacterial, anti-perspirant, astringent, and anti-fungal agents.

11. A spray dried body powder composition as in claim 10, wherein said biologically active agent is selected from the group consisting of bisabolol, tocopherol and farnesol.

12. A spray dried body powder composition as in claim 1, wherein said dry body powder has a water content of less than 5%.

* * * * *